United States Patent [19]

Engel

[11] 4,152,455

[45] May 1, 1979

[54] INSECTICIDAL α-TRIFLUOROMETHYL-3-PHENOXYBENZYL CARBOXYLATES

[75] Inventor: John F. Engel, Medina, N.Y.

[73] Assignee: FMC Corporation, Philadelphia, Pa.

[21] Appl. No.: 765,014

[22] Filed: Feb. 2, 1977

[51] Int. Cl.$^2$ ..................... C07C 69/74; A61K 31/215
[52] U.S. Cl. .................................... 424/305; 260/592; 424/306; 424/308; 560/105; 560/124; 568/637
[58] Field of Search ................. 560/124; 424/305, 306

[56] References Cited

FOREIGN PATENT DOCUMENTS

| | | |
|---|---|---|
| 801946 | 1/1974 | Belgium. |
| 2231312 | 1/1973 | Fed. Rep. of Germany. |
| 2407024 | 8/1974 | Fed. Rep. of Germany. |
| 2547534 | 4/1976 | Fed. Rep. of Germany. |
| 73/3528 | 5/1973 | South Africa. |

OTHER PUBLICATIONS

Brown, J. Arg. Food Chem., 23, 115 (1975).
Elliott, J. Sci. Fd. Agric., 18, 325 (1967).
Matsui, Agr. Biol. Chem., 31, 1143 (1967).
Matsuo, Arg. Biol. Chem., 40, 247 (1976).
Ohno, Arg. Biol. Chem., 38, 881 (1974).
Yoshioka, J. Kagaku To Seibutsu, 14, 427 (1976).
Melnikov, "Chemistry of Pesticides", pp. 1-11, (1971).
Burt, Pestic Sci., 5, pp. 791-799, (1975).

*Primary Examiner*—Bernard Helfin
*Assistant Examiner*—Michael Shippen
*Attorney, Agent, or Firm*—Richard L. Hansen; Henry R. Ertelt

[57] ABSTRACT

New insecticides, organic esters wherein the alcohol moiety is α-trifluoromethyl-3-phenoxybenzyl alcohol and the acid moiety is a pyrethroid carboxylic acid, are described and shown to control a broad spectrum of insects, including acarids.

7 Claims, No Drawings

INSECTICIDAL α-TRIFLUOROMETHYL-3-PHENOXYBENZYL CARBOXYLATES

BACKGROUND OF THE INVENTION

1. Field of the Invention

This invention pertains to the field of bioaffecting compositions; more specifically, it pertains to novel carboxylic acid esters and intermediates thereto, to insecticidal compositions containing the novel esters, and to the use of the compositions for controlling insects.

2. Description of the Prior Art

Pyrethrins have long been of interest as insecticides. Since it was discovered that pyrethrins are organic esters, various synthetic modifications have been made in the carboxylic acid and in the alcohol moieties on either side of the ester linkage to produce pyrethroid insecticides. Many of the synthetic pyrethroids are more effective than the natural pyrethrins, and recent modifications have overcome a chronic pyrethrins problem—instability to air and light.

The carboxylic acid moiety in the aforesaid esters has often been a 2,2-dimethyl-1-cyclopropanecarboxylic acid. Several important acids in this class contain substituents other than hydrogen in the 3-position. These 3-substituents include the 2,2-dimethylvinyl group, and the 2-carbomethoxy-2-methylvinyl group, found in the pyrethrins, the 2,2-dihalovinyl group, which appears in many of the recent stable pyrethroids [South African Pat. No. 73/3528], and simply 3,3-dimethyl substitution [Ger. Offen. No. 2,407,024]. It is not necessary that the acid moiety be a cyclopropanecarboxylic acid, however; 2-(4-chlorophenyl)-3-methylbutanoic acid is functionally similar in pyrethroids [Belg. Pat. No. 801.946]. All of these acids, those appearing as the acid moiety in the aforesaid pyrethrins and pyrethroids, are pyrethroid carboxylic acids, chemical structures well known to those skilled in the art.

Many variations in the alcohol moiety of the aforesaid esters have been disclosed also. These alcohols are described in the prior art and are well known. For example, pyrethroids wherein the alcohol moiety is an α-substutited-3-phenoxybenzyl alcohol have been disclosed [Ger. Offen. Nos. 2,231,312; 2,407,024; 2,547,534]. The relative insecticidal activity of a series of α-substituted-3-phenoxybenzyl carboxylates has been published [Matsuo, et al., Agr. Biol. Chem., 40, 247 (1976)]. The α-substituent, monochloromethyl, is disclosed by Matsuo, et al., but this appears to be the only α-haloalkylphenoxybenzyl alcohol moiety to appear in the aforesaid esters.

SUMMARY OF THE INVENTION

It has now been discovered that certain α-trifluoromethylphenoxybenzyl carboxylates are effective insecticides, characterized by long residual activity, which may be used to control a broad spectrum of insect pests, including acarids. The chemical structural formulae of the insecticidal α-trifluoromethylphenoxybenzyl carboxylates of this invention contain a pyrethroid carboxylic acid moiety and an α-trifluoromethylphenoxybenzyl alcohol moiety.

Although a large number of pyrethroid carboxylic acids are known in the art as outlines above and may be employed as the acid moiety in insecticidal esters, the insecticidal esters of this invention contain a pyrethroid carboxylic acid moiety selected from 2,2-dimethylcyclopropanecarboxylic acids and 2-(4-chlorophenyl)-3-methylbutanoic acid. When the acid moiety is a 2,2-dimethylcyclopropanecarboxylic acid, the 3-(2,2-dihalovinyl), 3-(2,2-dimethylvinyl), and 3,3-dimethyl-substituted compounds are favored. The 3-(2,2-dihalovinyl) compounds are especially useful, and 3-(2,2-dichlorovinyl)-2,2-dimethylcyclopropanecarboxylic acid is especially favored.

Although insecticidal esters may result from the combination of a pyrethroid carboxylic acid moiety and any isomeric α-trifluoromethylphenoxybenzyl alcohol moiety, α-trifluoromethyl-3-phenoxybenzyl alcohol is the alcohol moiety in the insecticidal esters of this invention.

Also within the contemplation of the instant invention are insecticidal compositions comprising a biologically effective amount of at least one insecticidal α-trifluoromethyl-3-phenoxybenzyl carboxylate as described hereinabove and a method of controlling insects, including acarids, which comprises applying to the locus where control is desired an insecticidally effective amount of at least one insecticidal α-trifluoromethyl-3-phenoxybenzyl carboxylate.

DETAILED DESCRIPTION OF THE INVENTION

Preparation of the α-trifluoromethyl-3-phenoxybenzyl carboxylates and intermediates of this invention, as well as insecticidal compositions containing the esters and use of the compositions for controlling insects, are illustrated in the following examples. Unless otherwise indicated, all temperatures are in degrees centigrade and pressures are in millimeters of mercury. Proton chemical shifts, taken from nmr spectra, are reported with respect to tetramethylsilane.

EXAMPLE I

PREPARATION OF α-TRIFLUOROMETHYL-3-PHENOXYBENZYL ALCOHOL

A. Synthesis of 1-Bromo-3-phenoxybenzene

To a stirred mixture of 23 g sodium methylate in 69 g methanol and 200 ml of 2-methoxyethyl ether (diglyme) at room temperature was added dropwise 40.0 g of phenol in a period of ½ hour. The reaction mixture was then heated to 165°, and 5.0 g cuprous bromide was added. The reaction mixture was cooled to 150° and 100.0 g of 1,3-dibromobenzene was added rapidly. Upon complete addition, the reaction mixture was warmed to 165° and stirred for 24 hours. The reaction mixture was then allowed to cool to room temperature and filtered. The filter cake was washed with two 75 ml portions of chloroform. The filtrate was dried with sodium sulfate and filtered. Chloroform was evaporated from the filtrate under reduced pressure, leaving a residue. The residue was distilled under reduced pressure to give 40.5 g of 1-bromo-3-phenoxybenzene; bp, 98°–100°/0.5 mm. The nmr and the ir spectra were consistent with the assigned structure.

B. Synthesis of 3-Phenoxy-α,α,α-trifluoroacetophenone

To a mixture of 3.6 g of magnesium turnings in 100 ml of dry diethyl ether at room temperature was added dropwise, under a dry nitrogen atmosphere, a solution of 35.0 g of 1-bromo-3-phenoxybenzene in 50 ml of dry diethyl ether; the addition was conducted at such a rate as to promote gentle reflux. Upon complete addition the reaction mixture was heated under reflux for ½ hour. The reaction mixture was then cooled to 5°, and a solution of 5.7 g trifluoroacetic acid in 25 ml of dry diethyl ether, also at 5°, was added dropwise. Upon complete addition, the reaction mixture was stirred for 1 hour, then heated under reflux for 1 hour. The reaction mixture was allowed to cool to room temperature over a period of 16 hours; then it was poured slowly into 200 ml of water. The alkaline solution (pH~10) was cooled in an ice bath, and approximately 150 ml of aqueous 10% hydrochloric acid was added, bringing the pH to approximately 3. The solution was extracted with three 150 ml portions of diethyl ether. The combined ether layers were washed with two 100 ml portions of an aqueous solution saturated with sodium bicarbonate, then with 200 ml of water. The ether layer was dried with sodium sulfate and filtered. The ether was evaporated from the filtrate under reduced pressure, leaving a liquid residue. The residue was distilled under reduced pressure to give 9.6 g of 3-phenoxy-$\alpha,\alpha,\alpha$-trifluoroacetophenone; bp, 62°–67°/0.03–0.04 mm.

C. Synthesis of $\alpha$-Trifluoromethyl-3-phenoxybenzyl Alcohol

To a stirred mixture of 1.6 g of lithium aluminum hydride in 10 ml of dry diethyl ether was added dropwise, at such a rate as to promote gentle reflux, a solution of 9.8 g of 3-phenoxy-$\alpha,\alpha,\alpha$-trifluoroacetophenone in 50 ml of dry diethyl ether. Upon complete addition, the reaction mixture was heated under reflux for 1 hour, then cooled to 5°. An additional 50 ml of "wet" ether was added dropwise, followed by the slow dropwise addition of 5 ml of cold water. The mixture was poured into 100 ml of an aqueous solution of 10% hydrochloric acid. The resulting mixture was extracted with three 100 ml portions of diethyl ether. The combined ether layers were washed with two 100 ml portions of an aqueous sodium bicarbonate solution, then with 100 ml of water. The ether layer was dried with sodium sulfate and filtered. The ether was evaporated from the filtrate under reduced pressure, leaving a liquid residue consisting of 9.9 g of $\alpha$-trifluoromethyl-3-phenoxybenzyl alcohol. The ir spectrum was consistent with the assigned structure.

Analysis: Calc'd for $C_{14}H_{11}F_3O_2$: C, 62.69; H, 4.13. Found: C, 62.99; H, 4.13.

nmr$\delta$ppm (CDCl$_3$): 2.90 (s,1H), 4.90 (q, 1H), 6.90–7.50 (m, 9H).

EXAMPLE II

PREPARATION OF
$\alpha$-TRIFLUOROMETHYL-3-PHENOXYBENZYL
3-(2,2-DICHLOROVINYL)-2,2-DIMETHYLCYCLOPROPANECARBOXYLATE To a stirred solution of 3.9 g of 3-(2,2-dichlorovinyl)-2,2-dimethylcyclopropanecarbonyl chloride, which may be prepared from the corresponding acid by the method described for the 2,2-difluorovinyl analog in *J. Agr. Food Chem.*, 23, 115 (1975), and 1.42 g of pyridine in 40 ml of toluene at 5° was added dropwise a solution of 4.6 g of $\alpha$-trifluoromethyl-3-phenoxybenzyl alcohol in 10 ml of toluene. The temperature of the reaction mixture was maintained at 5° during the addition. Upon complete addition, the reaction mixture was stirred at room temperature for 16 hours, then filtered. The filter cake was washed with toluene, and toluene was evaporated from the filtrate under reduced pressure, leaving an oil consisting of 8.0 g of $\alpha$-trifluoromethyl-3-phenoxybenzyl 3-(2,2-dichlorovinyl)-2,2-dimethylcyclopropanecarboxylate. The ir spectrum was consistent with the assigned structure.

Analysis: Calc'd for $C_{22}H_{19}Cl_2F_3O_3$: C, 57.53; H, 4.17; Cl, 15.44; F, 12.41. Found: C, 57.80; H, 4.45; Cl, 15.28; F, 12.68.

nmr$\delta$ppm (CDCl$_3$): 1.10 (s, 3H), 1.35 (s, 3H), 1.65–2.40 (m, 2H), 5.65–6.3 (m, 2H), 6.90–7.50 (m, 9H).

EXAMPLE III

PREPARATION OF
$\alpha$-TRIFLUOROMETHYL-3-PHENOXYBENZYL
3-(2,2-DIMETHYLVINYL)-2,2-DIMETHYLCYCLOPROPANECARBOXYLATE This compound was prepared in the manner of Example II using 3.3 g of 2,2-dimethyl-3-(2-methyl-1-propenyl)cyclopropanecarbonyl chloride, whose preparation is described in *J. Sci. Food and Agriculture*, 18, 325 (1967), 4.3 g of $\alpha$-trifluoromethyl-3-phenoxybenzyl alcohol, and 1.5 g of pyridine in 50 ml of toluene. Volatiles were distilled from the crude reaction product at 90°/0.08 mm for ½ hour, then at 100°/0.08 mm for ¾ hour through a short path Kugelrohr distillation system to give as a residue 6.3 g of $\alpha$-trifluoromethyl-3-phenoxybenzyl 3-(2,2-dimethylvinyl)-2,2-dimethylcyclopropanecarboxylate. The ir spectrum was consistent with the assigned structure.

Analysis: Calc'd for $C_{24}H_{25}F_3O_3$: C, 68.89; H, 6.02; F, 13.62. Found: C, 69.16; H, 6.02; F, 13.38.

nmr$\delta$ppm (CDCl$_3$): 1.10 (s,3H), 1.30 (s, 3H), 1.45–2.25 (m, 8H), 4.95 (d, 1H), 5.95–6.30 (q, 1H), 6.90–7.50 (m, 9H).

EXAMPLE IV

PREPARATION OF
$\alpha$-TRIFLUOROMETHYL-3-PHENOXYBENZYL
2,2,3,3-TETRAMETHYLCYCLOPROPANECARBOXYLATE This compound was prepared in the manner of Example II using 2.8 g of 2,2,3,3-tetramethylcyclopropanecarbonyl chloride, whose preparation is described in *Agr. Biol. Chem.*, 31, 1143 (1967), 4.0 g of $\alpha$-trifluoromethyl-3-phenoxybenzyl alcohol, and 1.5 g of pyridine in 50 ml of toluene. Volatiles were distilled from the crude reaction product at 110°/0.1 mm through a short path Kugelrohr distillation system to give a residue consisting of 3.9 g of $\alpha$-trifluoromethyl-3-phenoxybenzyl 2,2,3,3-tetramethylcyclopropanecarboxylate. The ir spectrum was consistent with the assigned structure.

Analysis: Calc'd for $C_{22}H_{23}F_3O_3$: C, 67.34; H, 5.91. Found: C, 67.55; H, 5.97.

nmr$\delta$ppm (CDCl$_3$): 1.15–1.25 (m, 13H), 6.15 (q, 1H), 6.9–7.6 (m, 9H).

EXAMPLE V

PREPARATION OF
$\alpha$-TRIFLUOROMETHYL-3-PHENOXYBENZYL
2-(4-CHLOROPHENYL)-3-METHYLBUTANOATE This compound was prepared in the manner of Example II, using 5.3 g of 2-(4-chlorophenyl)-3-methylbutanoyl chloride, whose preparation is described in *Agr. Biol. Chem.*, 38, 881 (1974), together with *J. Kagaku To Seibutsu*, 14, 427 (1976), 4.6 g of $\alpha$-trifluoromethyl-3- phenoxybenzyl alcohol, and 1.5 g of pyridine in 50 ml of toluene. Volatiles were removed from the crude reaction product at 100° C./0.02 mm through a short path Kugelrohr distillation system to give as a residue 7.8 g of α-trifluoromethyl-3-phenoxybenzyl 2-(4-chlorophenyl)-3-methylbutanoate. The ir spectrum was consistent with the assigned structure.

Analysis: Calc'd for $C_{25}H_{22}ClF_3O_3$: C, 64.87; H, 4.79; Cl, 7.66. Found: C, 65.07; H, 4.91; Cl, 8.20.

nmrδppm ($CDCl_3$): 0.60–1.10 (m, 6H), 2.10–2.60 (m, 1H), 3.30 (d, 1H), 5.90–6.30 (q, 1H), 6.90–7.40 (m, 13H).

In the normal use of the insecticidal esters of the present invention, the esters usually will not be employed free from admixture or dilution, but ordinarily will be used in a suitable formulated insecticidal composition compatible with the method of application and comprising a biologically effective amount of at least one insecticidal α-trifluoromethyl-3-phenoxybenzyl carboxylate. The insecticidal esters of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 10 parts of α-trifluoromethyl-3-phenoxybenzyl carboxylate, 30 parts of bentonite clay, and 60 parts of talc.

The esters of the present invention may be made into liquid concentrates by dissolution or emulsification in suitable liquids and into solid concentrates by admixture with talc, clays, and other known solid carriers used in the pesticide art. The concentrates are insecticidal compositions containing, as a biologically effective amount, about 5–50% α-trifluoromethyl-3-phenoxybenzyl carboxylate, such as α-trifluoromethyl-3-phenoxybenzyl 3-(2,2-dichlorovinyl)-2,2-dimethylcyclopropanecarboxylate, and 95–50% inert material, which includes surface-active dispersing, emulsifying, and wetting agents. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects contains 1.5 parts each of sodium lignosulfonate and sodium laurylsulfate as wetting agents, 25 parts of α-trifluoromethyl-3-phenoxybenzyl 2-(4-chlorophenyl)-3-methylbutanoate and 72 parts of bentonite clay.

Useful liquid concentrates include the emulsifiable concentrates, which are homogeneous liquid or paste compositions readily dispersed in water or other liquid carriers. They may consist entirely of the insecticide with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentration, such as acetone or other organic solvents.

A biologically effective amount of α-trifluoromethyl-3-phenoxybenzyl carboxylate in an insecticidal composition diluted for application is normally in the range of about 0.001% to about 2% by weight. Many variations of spraying and dusting compositions known in the art may be used by substituting the esters of this invention into compositions known or apparent to the art.

The insecticidal compositions of this invention may be formulated with other active ingredients, including other insecticides, nematicides, acaricides, fungicides, plant growth regulators, fertilizers, etc. In using the insecticidal compositions to control insects, it is only necessary that an insecticidally effective amount of at least one insecticidal α-trifluoromethyl-3-phenoxybenzyl carboxylate be applied to the locus where control is desired. For most applications, an insecticidally effective amount of α-trifluoromethyl-3-phenoxybenzyl carboxylate will be about 75 to 4000 g per hectare, preferably 150 g to 3000 g per hectare.

The insecticidal activity of the α-trifluoromethyl-3-phenoxybenzyl carboxylates of this invention was evaluated as follows:

EXAMPLE VI

Activity Against Crop Insects And Mites

The ester to be tested (0.25 g) was dissolved in 20 ml of acetone, and this solution was dispersed in 180 ml of water containing one drop of isooctyl phenyl polyethoxyethanol. Aliquots of this solution, containing 1250 ppm ester, were diluted with appropriate amounts of water to provide test solutions containing lesser amounts of the active ingredient.

Test organisms and techniques were as follows: Activities against the Mexican bean beetle (*Epilachna varivestis* Muls.) and the southern armyworm (*Spodoptera cridania* [Cram.]) were evaluated by dipping the leaves of pinto bean plants into the test solution and, when the foliage has dried, infesting the leaves with the appropriate immature insects; activity against the pea aphid (*Acyrthosiphon pisum* [Harris]) was evaluated on broad bean plants whose leaves were dipped before infestation with adult aphids; activity against twospotted spider mites (*Tetranychus urticea* Koch) was evaluated on pinto bean plants whose leaves were dipped after infestation with adult mites; activities against the milkweed bug (*Oncopeltus fasciatus* [Dallas]) and the plum curculio (*Conotrachelus nenuphar* [Herbst]) were evaluated by spraying the test solutions into glass dishes or jars containing the adult insects. All organisms in the tests were maintained in a holding room at 80° F. and 50% relative humidity for an exposure period of 48 hours. At the end of this time, the dead and living insects or mites were counted, and the percent kill was calculated. Results of these tests are summarized in Tables VI A and B.

The residual contact activity of the compounds was also determined on the same organisms using the techniques described above, except that in each case the treated surface was allowed to dry and was exposed to normal light and air for seven days before introduction of the mites or insects. The results of these tests also appear in Tables VI A and B as the figures in parenthesis.

The α-trifluoromethyl-3-phenoxybenzyl carboxylates are highly effective, both upon initial application and after exposure to light and air.

insects recovered. After confining the insects against nylon mesh at one end of the container, one microliter of an acetone solution containing a measured amount of the candidate insecticide was applied topically to each insect. The insects were then allowed to move freely about the container. Knockdown counts were recorded 10 minutes after treatment in the case of flies and 30 minutes after treatment in the case of cockroaches. Kill was recorded 18–24 hours after treatment. The results appear in Tables VII A and VII B.

High insecticidal activity against household insects is indicated, especially for α-trifluoromethyl-3-phenoxybenzyl 3-(2,2-dichlorovinyl)-2,2-dimethylcyclopropanecarboxylate.

TABLE VII A

ACTIVITY AGAINST HOUSE FLIES

| Compound of Example | Amount Applied (μg) | % Knockdown | % Kill |
|---|---|---|---|
| II | 5 | 0 | 100 |
|  | 1 | 0 | 100 |
|  | 0.5 |  | 77.6 |
|  | 0.4 |  | 57.8 |
|  | 0.3 |  | 38.5 |
|  | 0.2 |  | 10.3 |
| III | 5 | 15 | 85 |
|  | 1 | 5 | 10 |
| IV | 5 | 85 | 100 |
|  | 1 | 25 | 75 |
| V | 5 | 10 | 45 |

TABLE VI A

ACTIVITY OF α-TRIFLUOROMETHYL-3-PHENOXYBENZYL 3-(2,2-DICHLOROVINYL)-2,2-DIMETHYL-CYCLOROPANECARBOXYLATE AGAINST CROP INSECTS AND MITES

| Conc. ppm. | Percent Kill[a] | | | | | |
|---|---|---|---|---|---|---|
|  | Mexican Bean Beetle | Southern Armyworm | Pea Aphid | Twospotted Spider Mite | Milkweed Bug | Plum Curculio |
| 1250 |  |  |  | (21) | 100 (100) | (100) |
| 625 |  |  | (100) | 80 | (100) |  |
| 312 |  | (100) | (100) | 84 | 80 (100) | 0 |
| 156 |  | ( 95) | ( 19) | 58 | ( 30) |  |
| 78 |  | (100) | ( 17) | 11 | 0 ( 25) | 45 |
| 39 |  | ( 35) | 57 |  |  |  |
| 20 | ( 76) |  | 0 |  |  |  |
| 10 | 100 ( 63) | 85 | 6 |  |  |  |
| 5 | ( 10) | 40 | 0 |  |  |  |
| 2.5 | 95 ( 0) |  |  |  |  |  |
| 1.2 | 90 |  |  |  |  |  |
| 0.6 | 90 |  |  |  |  |  |
| 0.3 | 50 |  |  |  |  |  |

[a]The figures in parenthesis refer to residual contact activity 7 days after treatment.

TABLE VI B

ACTIVITY OF α-TRIFLUOROMETHYL-3-PHENOXYBENZYL 2-(4-CHLOROPHENYL)-3-METHYLBUTANOATE AGAINST CROP INSECTS AND MITES

| Conc. ppm. | Percent Kill[a] | | | | | |
|---|---|---|---|---|---|---|
|  | Mexican Bean Beetle | Southern Armyworm | Pea Aphid | Twospotted Spider Mite | Milkweed Bug | Plum Curculio |
| 1250 | 100 (100) | 100 ( 95) | 100 (100) | 95.8 (1.1) | 89 ( 55) | 0 ( 0) |
| 625 |  |  | (100) |  | ( 25) | ( 0) |
| 312 | 100 (100) | 89 ( 15) | 60 ( 71) | 64 | 5 ( 0) | 5 ( 0) |
| 78 | (100) | ( 10) |  |  |  |  |
| 39 | 100 | 21 | 40 | 1.8 | 0 | 10 |
| 10 | 100 | 50 | 38 | 1.7 | 0 | 5 |
| 2.5 | 67 | 0 |  |  |  |  |

[a]The figures in parenthesis refer to residual contact activity 7 days after treatment.

EXAMPLE VII

Activity Against Household Insects

The insecticidal esters of this invention were evaluated against cockroaches and house flies as follows: 20 resistant female house flies [*Musca domestica* Linnaeus] or 10 male cockroaches [*Blattella germanica* Linnaeus] were anesthetized with carbon dioxide and placed in a container for about 2 hours, during which time the

TABLE VII B
ACTIVITY AGAINST GERMAN COCKROACHES

| Compound of Example | Amount Applied (μg) | % Knockdown | % Kill |
|---|---|---|---|
| II | 5 | 0 | 100 |
|  | 1 | 0 | 40 |
| III | 5 | 0 | 10 |
|  | 1 | 0 | 0 |
| IV | 5 | 0 | 90 |
|  | 1 | 0 | 0 |
| V | 5 | 0 | 20 |

EXAMPLE VIII

Activity Against Mosquito Larvae

The esters of this invention at various concentrations in acetone/water solution were tested against live mosquito larvae [*Aedes aegypti*] placed in the solutions. The number of dead larvae was determined after 24 hours and after 1 week. The results appear in Table VIII.

The α-trifluoromethyl-3-phenoxybenzyl carboxylates are very effective against mosquito larvae, even at low concentrations.

TABLE VIII
ACTIVITY AGAINST MOSQUITO LARVAE

| Compound of Example | Concentration (ppm) | % Kill (24 Hr.) | % Kill (7 Days) |
|---|---|---|---|
| II | 10 | — | 100 |
|  | 1 | 100 | 100 |
|  | 0.1 | 100 | 100 |
|  | 0.01 | 100 | 100 |
| III | 10 | — | 100 |
|  | 1 | 100 | 100 |
|  | 0.1 | 90 | 100 |
|  | 0.01 | 15 | 25 |
| IV | 10 | — | 100 |
|  | 1 | 100 | 100 |
|  | 0.1 | 95 | 100 |
|  | 0.01 | 45 | 75 |
| V | 10 | — | 100 |
|  | 1 | 70 | 100 |
|  | 0.1 | 30 | 95 |
|  | 0.01 | 10 | 15 |

EXAMPLE IX

Ovicidal Activity Against the Twospotted Spider Mite

Pinto bean seedlings were infested with female twospotted spider mites. After allowing 3-4 hours for egg deposition, the plants were dipped into a solution containing 936 ppm TEPP (tetraethyl pyrophosphate). TEPP kills motile forms on the leaf and promptly degrades without affecting the egg stage. 2-3 Hours after the TEPP treatment, the plants were dipped into an acetone/water insecticide solution. The test plants were maintained for 7-10 days, termination of the test being determined by the time required to attain complete hatch in an untreated control experiment. In Table IX are recorded the results of these experiments.

The esters of this invention are toxic to mite eggs.

TABLE IX
OVICIDAL ACTIVITY AGAINST THE TWOSPOTTED SPIDER MITE

| Compound of Example | Concentration (ppm) | % Egg Kill |
|---|---|---|
| II | 1250 | 100 |
|  | 312 | 94 |
| V | 1250 | 58 |
|  | 312 | 0 |
|  | 39 | 0 |

It is apparent that many modifications may be made in the formulation and application of the insecticidal esters of this invention, without departing from the spirit and scope of the invention and of the following claims.

I claim:

1. An insecticidal α-trifluoromethyl-3-phenoxybenzyl carboxylate whose chemical structural formula consists of a 2,2-dimethylcyclopropanecarboxylic acid selected from 3-(2,2-dihalovinyl)-2,2-dimethylcyclopropanecarboxylic acids, 3-(2,2-dimethylvinyl)-2,2-dimethylcyclopropanecarboxylic acid and 2,2,3,3-tetramethylcyclopropanecarboxylic acid esterified with α-trifluoromethyl-3-phenoxybenzyl alcohol.

2. A chemical compound according to claim 1 wherein the 2,2-dimethylcyclopropanecarboxylic acid is a 3-(2,2-dihalovinyl)-2,2-dimethylcyclopropanecarboxylic acid.

3. The chemical compound of claim 1 wherein the 3-(2,2-dihalovinyl)-2,2-dimethylcyclopropanecarboxylic acid is 3-(2,2-dichlorovinyl)-2,2-dimethylcyclopropanecarboxylic acid.

4. An insecticidal composition comprising an insecticidally effective amount of at least one insecticidal α-trifluoromethyl-3-phenoxybenzyl carboxylate of claim 1 in admixture with an agriculturally acceptable carrier.

5. A method of controlling insects, including acarids, which comprises applying to the locus where control is desired an insecticidally effective amount of at least one insecticidal α-trifluoromethyl-3-phenoxybenzyl carboxylate of claim 1.

6. An insecticidal composition comprising an insecticidally effective amount of the compound of claim 3 in admixture with an agriculturally acceptable carrier.

7. A method of controlling insects, including acarids, which comprises applying to the locus where control is desired an insecticidally effective amount of the compound of claim 3.

* * * * *